(12) United States Patent
Hamill et al.

(10) Patent No.: US 9,456,791 B2
(45) Date of Patent: Oct. 4, 2016

(54) SYSTEM AND METHOD FOR CONSTRAINING A COMPUTERIZED TOMOGRAPHY PATIENT

(75) Inventors: James J. Hamill, Knoxville, TN (US); Carl Eric Arnsdorff, Knoxville, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1898 days.

(21) Appl. No.: 12/558,159

(22) Filed: Sep. 11, 2009

(65) Prior Publication Data

US 2010/0063378 A1    Mar. 11, 2010

Related U.S. Application Data

(60) Provisional application No. 61/095,983, filed on Sep. 11, 2008, provisional application No. 61/095,981, filed on Sep. 11, 2008.

(51) Int. Cl.
| | | |
|---|---|---|
| A61G 15/00 | (2006.01) | |
| A61B 6/03 | (2006.01) | |
| A61B 6/04 | (2006.01) | |
| A61B 5/103 | (2006.01) | |
| A61B 6/00 | (2006.01) | |

(52) U.S. Cl.
CPC ............. *A61B 6/037* (2013.01); *A61B 6/0421* (2013.01); *A61B 5/103* (2013.01); *A61B 6/482* (2013.01)

(58) Field of Classification Search
CPC .... A61B 5/0555; A61B 5/702; A61B 6/032; A61B 6/04; A61B 6/0421; A61F 5/37; A61F 5/3769; A61F 2007/0288; A61F 2007/0228
USPC ........ 128/845, 846, 869, 870, 877; 600/407, 600/415; 5/601; 378/20
See application file for complete search history.

(56) References Cited

U.S. PATENT DOCUMENTS

| | | | | |
|---|---|---|---|---|
| 3,545,739 A | * | 12/1970 | Avignon | ........................... 5/601 |
| 4,484,571 A | * | 11/1984 | Velazquez | ........................ 5/601 |
| 5,848,449 A | * | 12/1998 | Hauger et al. | .................... 5/637 |
| 2002/0134390 A1 | * | 9/2002 | Salatka et al. | ................ 128/857 |
| 2002/0196906 A1 | * | 12/2002 | Mun et al. | ..................... 378/206 |
| 2005/0083207 A1 | * | 4/2005 | Smith et al. | .................. 340/668 |
| 2006/0235291 A1 | * | 10/2006 | Haider et al. | ................. 600/415 |

* cited by examiner

*Primary Examiner* — Alireza Nia
*Assistant Examiner* — Caitlin Carreiro

(57) ABSTRACT

A constraint having a main body and at least one coupler. The main body can be substantially arcuate in shape and can be configured to constrain a patient. The at least one coupler can couple the main body to a bed or treatment pallet. The constraint can be sized to restrict a patient within a computerized tomography (CT) scan field of view.

20 Claims, 3 Drawing Sheets

SYSTEM AND METHOD FOR CONSTRAINING A COMPUTERIZED TOMOGRAPHY PATIENT

PRIORITY CLAIM

This application claims priority to and incorporates by reference, in their entirety, U.S. Provisional 61/095,981 and U.S. Provisional 61/095,983, both filed on Sep. 11, 2008.

FIELD

This disclosure, in a broad sense, is directed toward a constraint for constraining a patient during a medical procedure, for example an imaging process. The disclosure further relates to a constraint for constraining a patient within a range of fifty (50) to sixty (60) centimeters during a computerized tomography (CT) scanning.

BACKGROUND

Positron Emission Tomography (PET), Single Photon Emission Computed Tomography (SPECT), and Computed Axial Tomography (CT) are three medical imaging modalities. PET, SPECT and CT are popular in medicine because of their ability to non-invasively study both physiological processes and structures within the body. To better utilize PET, SPECT and CT, recent efforts have been made to combine either a SPECT scanner with a CT scanner or a PET scanner with a CT scanner into a single system. The combination of PET and CT or of SPECT and CT allows for better registration of the metabolic or functional PET or SPECT images with the anatomic CT image and for improved hospital workflow. The combined scanners share space within the same system housing and share a common patient bed or gurney, but use separate detectors and associated hardware. In the case of the PET/CT scanner, see e.g., U.S. Pat. No. 6,449,331, issued to Nutt, et al., on Sep. 10, 2002, entitled "Combined PET and CT Detector and Method for Using Same," which discloses a combined PET and CT scanner, and which is incorporated herein by reference in its entirety.

PET and SPECT are nuclear medicine imaging techniques used in the medical field to assist in the diagnosis of diseases. In both cases medical images are regenerated based on radioactive emission data, typically in the form of gamma rays, emitted from the body of a patient after the patient has ingested or been injected with a radioactive substance. PET and SPECT allow the physician to examine large sections of the patient at once and produce pictures of many functions of the human body unobtainable by other imaging techniques. In this regard, PET and SPECT display images of how the body works (physiology or function) instead of simply how it looks (anatomy or structure).

Mechanically, a PET or SPECT scanner consists of a bed (or treatment pallet) and a gantry, which is typically mounted inside an enclosure with a tunnel through the center, through which the bed traverses. The patient, who has been infused with a radiopharmaceutical, lies on the bed, which is then inserted into the tunnel formed by the gantry. In the case of SPECT, the gantry is rotated around the patient as the patient passes through the tunnel. The rotating gantry constrains the detectors and a portion of the processing equipment.

In the case of SPECT, emitted gamma rays are detected from numerous different projection angles by a gamma camera (in most cases, an Anger camera or scintillation camera) about a longitudinal axis of the patient, and converted into electrical signals that are stored as image data. Data from image projections provide a set of images as a result of a process known as image reconstruction. In the case of PET, the scanner detectors are designed to detect simultaneous and oppositely traveling gamma ray pairs from positron annihilation events within the patient. The injected or ingested radiopharmaceutical constrains positron-emitting atoms. The positrons annihilate with electrons in the patient to produce pairs of gamma rays where each member of the pair moves in an opposite direction. The paired gamma rays generate signals when they strike the PET scanner detectors. Signals from the gantry are fed into a computer system where the data is then processed to produce images as a result of a process known as image reconstruction.

PET is considered the more sensitive of the two nuclear medicine imaging techniques, and exhibits the greatest quantification accuracy, of any nuclear medicine imaging instrument available at the present time. Applications requiring this sensitivity and accuracy include those in the fields of oncology, cardiology, and neurology.

Another known tomography system is computed axial tomography (CAT, or now also referred to as CT, XCT, or x-ray CT). In CT, an external x-ray source is caused to be passed around a patient. Detectors on the other side of the patient from the x-ray source then respond to the x-ray transmission through the patient to produce an image of the area of study. Unlike SPECT or PET, which are emission tomography techniques because they rely on detecting radiation emitted from inside the patient, CT is a transmission tomography technique which utilizes a radiation source external to the patient. CT provides images of the internal structures of the body, such as the bones and soft tissues, whereas SPECT and PET provide images of the functional aspects, such as metabolism, of the body, usually corresponding to an internal organ or tissue.

Unlike the pairs of PET scanner detectors required to detect the gamma ray pairs from an annihilation event or the detector heads of the SPECT scanner, the CT scanner requires detectors mounted opposite an x-ray source. In third-generation computed tomography systems, the CT detectors and x-ray source are mounted on diametrically opposite sides of a gantry which is rotated around the patient as the patient traverses the tunnel.

The x-ray source emits a beam of x-rays which pass through the patient and are received by an array of detectors. As the x-rays pass through the patient, they are absorbed or scattered as a function of the densities of objects in their path. The output signal generated by each detector is representative of the x-ray attenuation of all objects between the x-ray source and the detector.

The medical images provided by the SPECT/CT scanner or by the PET/CT scanner are diagnostically complementary, and it is advantageous medically to have images of the same region of a patient from both emission and transmissions scans. To be most useful, the SPECT and CT images or the PET and CT images need to be correctly overlaid or co-registered such that the functional features in the PET images can be correlated with the structural features, such as bones, tumors, and lung tissue, in the CT images. Moreover, an accurate measurement of radiopharmaceutical uptake requires a corresponding accurate measurement of the location and attenuation properties of body tissues that lie along the lines of response used in the PET or SPECT measurement. The potential to combine functional and anatomical images is a powerful one, and there has been significant progress in the development of multi-modality image co-registration and alignment techniques. However, with the exception of the brain, the co-alignment of images from different modalities is not straightforward or very accurate, even when surface markers or reference points are used. To this end, it is desirable to incorporate SPECT and CT scanners or PET and CT scanners into a single gantry, thereby allowing the image data to be acquired sequentially or possibly simultaneously within a short period of time on the same patient table and overcoming alignment problems due to patient movement or internal organ movement such as caused by cancer treatment, respiration, variations in scanner bed profile, positioning of the patient for the scan, and other temporal changes in the patient.

As is well-known, compared to anatomical imaging modalities, SPECT images are photon-limited and generally lack anatomical landmarks, thus making image alignment, and the definition of regions-of-interest, even more of a problem than it is for PET. In addition, nonuniform photon attenuation introduces distortions and artifacts into the reconstructed images. As a result, hybrid CT/SPECT scanners have been developed to address these issues, see e.g., T. F. Lang et al., "A prototype emission-transmission imaging system," IEEE Nucl. Sci. Symposium Conf. Record 3, 1902-1906 (1991); and T. F. Lang et al., "Description of a prototype emission transmission computed tomography imaging system," J. Nucl. Med. 33, 1881-1887 (1992). In such a hybrid system, it is suggested to use the X-ray CT image to provide the attenuation factors to correct the SPECT data, see e.g., J. S. Fleming, "A technique for using CT images in attenuation correction and quantification in SPECT," Nucl. Med. Commun. 10, 83-97 (1989). The use of CT images for attenuation correction had been originally proposed by S. C. Moore, "Attenuation compensation" in Ell, P. J. et al., Computed Emission Tomography, London, Oxford University Press, 339-360 (1982). The 100 kVp X-ray source is capable of producing a dual-energy X-ray beam, such that an energy-corrected attenuation map can be obtained for use with the radionuclide data, as disclosed by B. H. Hasegäwa et al., "Object specific attenuation correction of SPECT with correlated dual-energy X-ray CT," IEEE Trans. Nucl. Sci. NS-40 (4), 1242-1252 (1993). Operating the device with two energy windows also allows simultaneous emission-transmission acquisitions to be performed, although the authors report a certain level of contamination of the emission scan by the transmission X-ray beam. This disclosure demonstrates the potential of a device capable of performing both anatomical and functional measurements. It has also given rise to a detailed simulation study to investigate the different techniques for scaling the attenuation coefficients from CT energies (50-80 keV) to SPECT (140 keV). See K. J. LaCroix et al., "Investigation of the use of X-ray CT images for attenuation compensation in SPECT," IEEE 1993 Medical Imaging Conference Record (1994). Similarly, CT images can be used for attenuation correction in PET images. (See, e.g., U.S. Patent Application 2004/0030246 by Townsend et al., which is incorporated in its entirety herein).

While the attenuation correction for PET is of a greater magnitude than for SPECT, it is theoretically more straightforward. However, since it is generally based on patient measurements (a transmission scan), it introduces additional noise into the reconstructed emission scan. In practice, in order to limit the duration of the PET scan procedure, abdominal transmission scans of 10-15 minutes are typical, during which 100 million counts are acquired (3 million per slice, or 100 counts per coincidence line of response, i.e. a 10% statistical accuracy), which introduces significant noise into the corrected emission scan. In practice, only lines-of-response (LOR's) through the patient constrain useful transmission information, and since some of the coincidence events will lie in LOR's which do not pass through the patient, the total useful counts in a transmission scan is often less than 100 million. In addition, patient movement between the transmission and emission scan (which may be acquired 40 minutes or so later) can introduce serious artifacts and distortions into the reconstructed image, as disclosed by S. C. Huang et al., "Quantitation in positron emission tomography: 2. Effects of inaccurate attenuation correction," J Comput Assist Tomogr 3, 804-814 (1979).

Inaccurate attenuation correction can increase when a patient extends beyond the field of view during CT measurements. For example, obese patients can receive cardiac PET/CT scanning procedures. As shown in FIG. 1, a CT section of an obese female is shown with the anatomy being well visualized within the FOV of the CT with gray values being fairly quantitative. However, outside the FOV of the CT, the edges are mis-positioned and CT values can be in error, which can lead to errors in the PET attenuation correction. The arrows in FIG. 1 point to regions with a pronounced truncation artifact. Typically, these problems are not present when the patient is within the FOV of the CT as shown in FIG. 2. To compensate for the problems associated when a patient is not within the FOV of the imaging system, software can be used to reduce the errors, e.g., extended field of view reconstruction method (EFOV). Although, the software assists in reducing the errors, the corrections only approximates the actual image outside the FOV and degrades the more a patient extends further outside the FOV.

BRIEF DESCRIPTION OF THE DRAWINGS

In order to facilitate a fuller understanding of the exemplary embodiments, reference is now made to the appended drawings. These drawings should not be construed as limiting, but are intended to be exemplary only.

DETAILED DESCRIPTION

The functions described as being performed at various components can be performed at other components, and the various components can be combined and/or separated. Other modifications also can be made.

Figure 1:
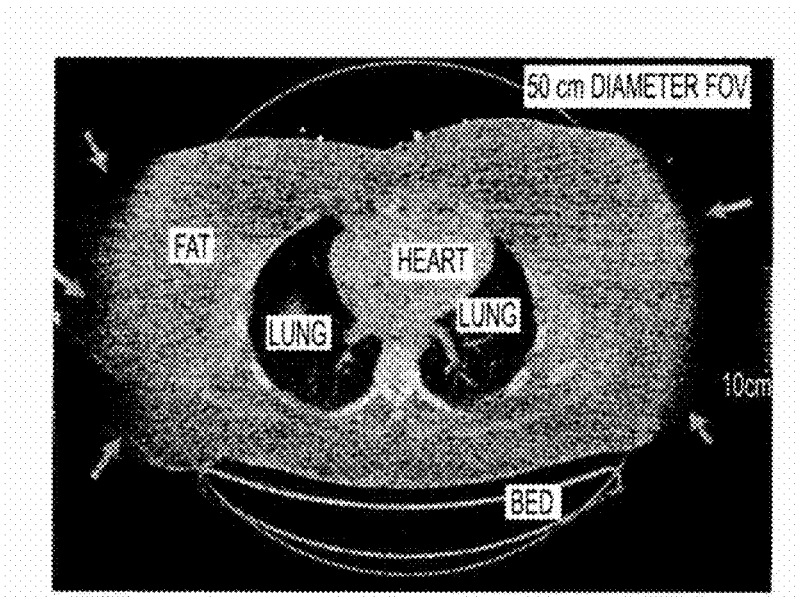
FIG. 1 is a CT image of a patient who extends out of the CT FOV.
Figure 2:
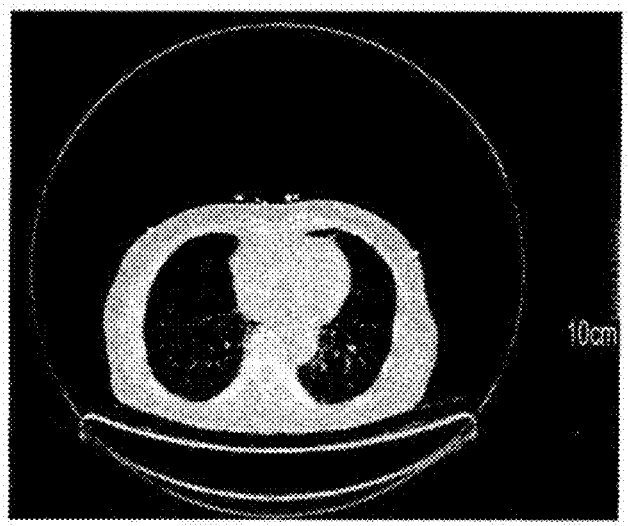
FIG. 2 is a CT image of a patient who does not extend out of the CT FOV.
Figure 3:
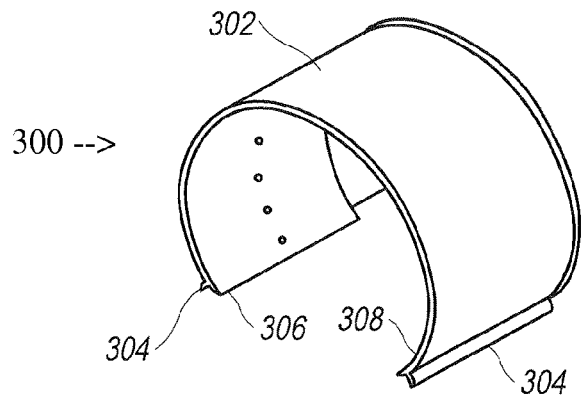
FIG. 3 is a front perspective view of the constraint in accordance with an exemplary embodiment.

Referring to FIG. 3, a front perspective of the constraint in accordance with an exemplary embodiment is illustrated. As shown, the constraint 300 can include a main body 302 and couplers 304. The main body 302 can be substantially arcuate in shape and rigid. The main body 302 can form an opening at the distal ends of the main body 302. For example, the opening can be formed between a first end 306 and a second end 308. The couplers 304 can be positioned at about each distal end of the main body 302, e.g., at the first end 306 and at the second end 308.

Figure 4:
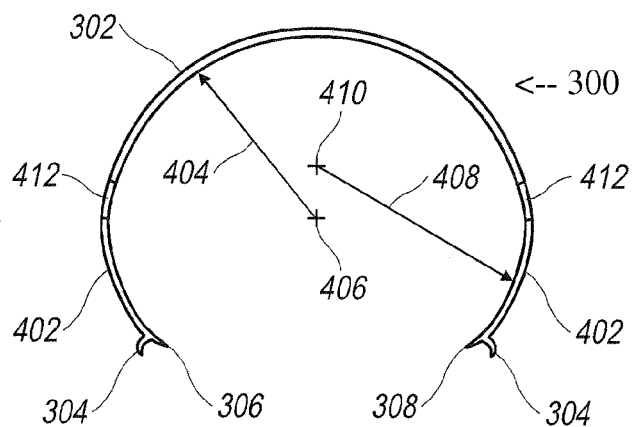
FIG. 4 is a front (or rear) view of the constraint in accordance with an exemplary embodiment.

Referring to FIG. 4, a front (or rear) view of a constraint in accordance with an exemplary embodiment is illustrated. As shown, the main body 302 can include two secondary sections 402. The secondary sections 402 can be located towards the distal ends of the main body 302, e.g., the first end 306 and the second end 308. The constraint 300 can be made of two arcs, one for the main body 302 and the other arc for the secondary sections 402. The two arcs can have the same radiuses. As shown in FIG. 4, the main body 302 can have a first radius 404 from a first center point 406 and the secondary sections 402 can have a second radius 408 from a second center point 410. The two center points 406, 410 can represent the center of the constraint 300 with the height of the patient in a scanning system being adjusted up and down, e.g., within a range, to accommodate the patient fitting into the scanning system. The first center point 406 can be where the bottom of the constraint 300, e.g., the secondary sections 402, constrains the patient when the patient is positioned at the lowest height within a scanning system. The second center point 410 can be where the top of the constraint 300, e.g., the main body 302, constrains the patient when the patient is positioned at the highest height within a scanning system. The first radius 404 and/or second radius 408 can be a constant or can vary. The first radius 404 and the second radius 408 can be substantially equal. As discussed in further detail below, in a first embodiment, the first radius 404 can be about twenty-five centimeters (25 cm, matching the measured field of view of most commercial CT scanners) and in a second embodiment, the first radius 404 can be about thirty centimeters (30 cm).

Figure 5:
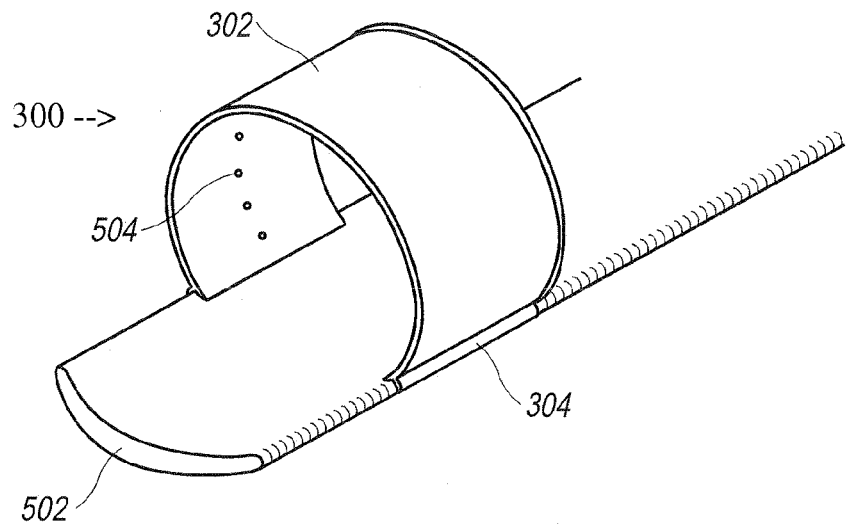
FIG. 5 is a front perspective view of the constraint coupled to a bed in accordance with an exemplary embodiment.

Referring to FIG. 5, a front perspective view of a constraint attached to a bed in accordance with an exemplary embodiment is illustrated. As shown, the couplers 304 can attach the constraint 300 to the bed 502 or a treatment pallet (not shown). A treatment pallet can be positioned on a bed 502 and can assist in positioning a patient to limit the patient from moving during a scan. As shown, the coupler 304 can be configured to snap onto the bed 502 or treatment pallet. The couplers 304 can be any suitable attachment that can attach and detach (e.g., detachably attach) the constraint 300 to the bed 502 or treatment pallet. In one or more embodiments, an end (e.g., the first end 306 or second end 308) can be pivotally attached to the bed 502 or treatment pallet with the other end having a coupler 304. In one or more embodiments, a strap (not shown) can be used to secure the constraint 300 to the bed 502 or treatment pallet. The strap can be fixedly attached to a side of the bed 502 or treatment pallet at one end, extend over the exterior of the constraint 300 and attach to the other side of the bed 502 or treatment pallet. The strap can attach to the side of the bed 502 or treatment pallet using a fastener such as a Velcro™ hook-and-loop fastener or other suitable attachments.

The constraint 300 can include a plurality of sensors 504 with each sensor 504 configured to provide an indication in response to a patient touching the sensor 504. The plurality of sensors 504 can be positioned on the constraint 300, e.g., on the internal side of the main body 302 and secondary sections 402. The sensors 504 can be contact sensors or any other suitable sensor to detect part of a patient that is in close proximity to the sensor 504.

The main body 302 and secondary sections 402 can be separate components or can be a unibody. The secondary sections 402 can be attached to the main body 302 at attachment points 412 as shown in FIG. 4. The couplers 304 and secondary sections 402 can be separate components or can be a unibody. The main body 302, couplers 304 and/or secondary sections 402 can be made of a material that allows x-rays and annihilation radiation to shine through the constraint 300 with minimum or low attenuation. Attenuation factors of 5% or less are desired. For example, the material can be carbon fiber or polyethylene.

Figure 6A:
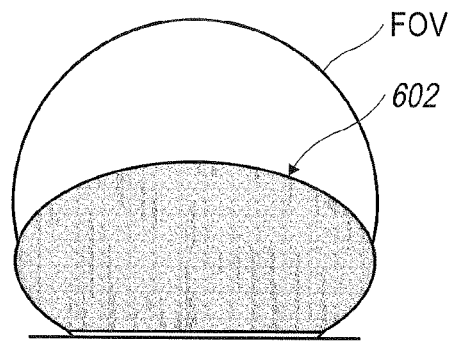
FIG. 6A is a block diagram of a patient who is not constrained within a FOV in accordance with conventional imaging systems.
Figure 6B:
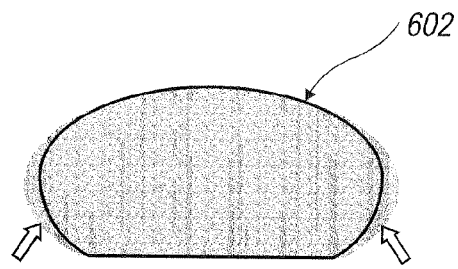
FIG. 6B is a block diagram of an image of a patient who is not constrained within a FOV in accordance with conventional imaging systems.

Referring to FIGS. 6A and 6B, block diagram of a patient, and an image of the patient, respectively, who is not constrained within a FOV in accordance with conventional systems are illustrated. As shown in FIG. 6A, the patient 602 extends outside of a FOV of an imaging system. For example, the patient 602 extends beyond the fifty centimeter (50 cm) FOV of a CT system. As a result, when the image of the patient 602 is generated by the imaging system, e.g., as shown in FIG. 6B, the image may not be as clear on the edges (e.g., "fuzzy edges") due to the imaging system having to approximate those areas. The more a patient extends out of the FOV of the imaging system, the greater the approximations and errors. For combined imaging systems, e.g., PET/CT or SPECT/CT systems, where images are combined, error corrections detected in the CT system are used to correct the PET or SPECT data using attenuation corrections. Thus when there are errors in the CT data, this can cause additional errors in the combined images of a patient 602 who extends outside of the FOV of the CT system.

Figure 7A:
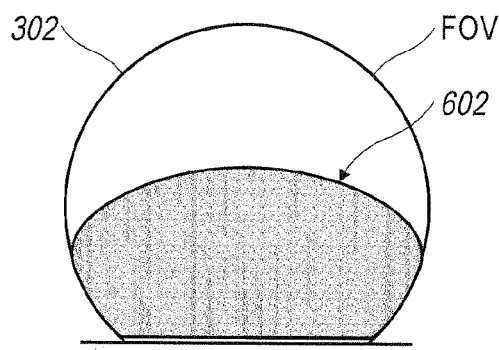
FIG. 7A is a block diagram of a patient who is constrained within a FOV by a constraint in accordance with an exemplary embodiment.
Figure 7B:
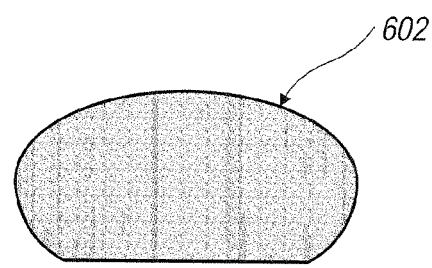
FIG. 7B is a block diagram of an image of a patient who is constrained within a FOV by a constraint in accordance with an exemplary embodiment.

Referring to FIGS. 7A and 7B, block diagrams of a patient, and an image of the patient, respectively, who is constrained within a FOV, in accordance with exemplary embodiments are illustrated. As shown in FIG. 7A, the constraint 300 can be sized to constrain a patient 602 within the FOV of the scanning system. For example, the constraint 300 can be sized to have a first radius 404 and/or second radius 408 of about twenty-five centimeters (25 cm) which is the FOV for a CT system. By constraining the patient 602 within the FOV, an imaging system can avoid a truncation process since the patient's body does not extend beyond the FOV. The imaging system can set any values outside of the FOV to zero since any such data is known to be inaccurate. As shown in FIG. 7B, the image of the patient 602 can be formed without substantial artifacts compared to an image of the same patient without a constraint, e.g., as shown in FIG. 6B described above.

Figure 8A:
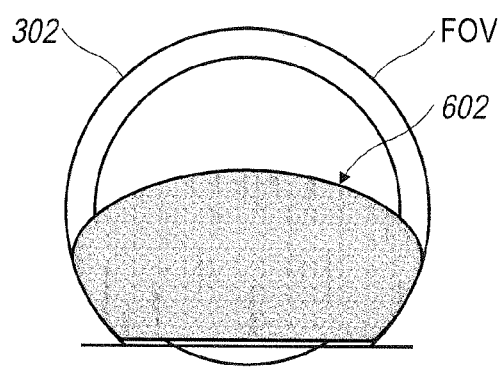
FIG. 8A is a block diagram of a patient who is not constrained within a FOV but is constrained by a constraint in accordance with an exemplary embodiment.
Figure 8B:
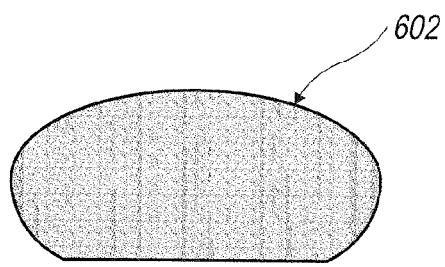
FIG. 8B is a block diagram of an image of a patient who is not constrained within a FOV but is constrained by a constraint in accordance with an exemplary embodiment.

Referring to FIGS. 8A and 8B, block diagrams of a patient, and an image of the patient, who is not constrained in a FOV of the imaging system but is constrained in a constraint, in accordance with exemplary embodiments are illustrated. For example, as shown in FIG. 8A, the constraint 300 can be sized to have a first radius 404 and/or second radius 408 of about thirty centimeters (30 cm) which is larger than the FOV for a CT system. Although the patient 602 is not constrained within the FOV of the imaging system, the patient 602 is constrained within the constraint 300. For example, the constraint can have a known radius of thirty centimeters (30 cms) and the imaging system can compensate for the area between the FOV and constraint 300 using an iterative reconstruction algorithm, such as the one disclosed in U.S. Patent Application 2008/0219534 by Faul et al. FIG. 8B illustrates a block diagram of an image of a patient 602 created using an iterative reconstruction algorithm. Using sensors 504 on the constraint 300 can also improve the images. For example, knowing where a patient 602 touches a sensor 504, the imaging system can "fill-in" the values for the area between the FOV of the imaging system and the constraint 300 with values appropriate for human adipose tissue. This can be done because the sensors 504 can provide an indication that part of the patient 602 is in close proximity to the sensor. Comparing FIGS. 6B and 8B, the image in FIG. 6B contains fuzzy edges and the image in 8b does not contain the fuzzy edges due to the reconstruction algorithm and/or filling in of the values of the human adipose tissue.

In imaging systems in which the constraint 300 is used, the constraint 300 has a known shape and location, thus the imaging system can account for the constraint 300. For example, the imaging system can mathematically model the constraint 300 and remove the constraint 300 from images that are generated.

The following describes exemplary methods in using the constraint 300 described above. A patient 602 can be prepped for imaging. This can include the patient 602 ingesting or being injected with a radiopharmaceutical substance. The patient 602 can be placed on a bed 502 or treatment pallet with gating leads and intravenous tubes attached. The constraint 300 can then be fastened to one side of the bed 502, placed over the patient 602 and fastened to the other side of the bed 502. The patient 602 can then be placed in a scanning system, e.g., a SPECT, PET, CT, SPECT/CT, PET/CT, or any other suitable imaging system. The imaging system can scan or image the patient 602. If the constraint 300 is about the same size as the FOV of the imaging systems, then the imaging system can ignore or eliminate data outside of the FOV of the imaging system. If the constraint 300 is greater than the FOV of the imaging system, the imaging system can use an iterative reconstruction algorithm to correct the artifacts in this region. In addition, if the constraint 300 includes sensors 504, the imaging system can use indications from the sensors to determine where parts of the patient 602 are located within the area between the FOV and the constraint 300 and fill-in these areas with values appropriate for human adipose tissue. The processing described above can be performed on the CT data (or image) to reduce the amount of artifacts and reduce errors associated with the artifacts, thereby increasing the effectiveness of the imaging system. For example, by reducing the artifacts in the CT data, the imaging system can improve the attenuation factors to correct the SPECT data or PET data.

In the preceding specification, various preferred embodiments have been described with reference to the accompanying drawings. It will, however, be evident that various modifications and changes can be made thereto, and additional embodiments can be implemented, without departing from the broader scope of the invention as set forth in the claims that follow. The specification and drawings are accordingly to be regarded in an illustrative rather than restrictive sense.

What is claimed is:

1. A constraint to constrain a patient with respect to a field of view of a medical imaging procedure, the constraint comprising:
   a main body having a substantially arcuate shape, a first end, and second end, said main body being adapted to constrain said patient to lie within a determinable area with respect to said field of view, so as to reduce artifacts in image reconstruction; and
   at least one coupler at about one of the first end or second end of the main body with said coupler adapted to attach the constraint to a bed or treatment pallet prior to the medical imaging procedure.

2. The constraint of claim 1 wherein the main body further comprises a main section having a first radius and two secondary sections having a second radius, with the main body interposed between the two secondary sections with the at least one coupler at about a distal end of one of the secondary sections.

3. The constraint of claim 2 wherein the first radius is in the range of about twenty-five (25) to thirty (30) centimeters.

4. The constraint of claim 2 wherein the second radius is in the range of about twenty-five (25) to thirty (30) centimeters.

5. The constraint of claim 2 wherein the first radius of the constraint is sized to restrict a patient to lie within a field of view of said medical imaging procedure.

6. The constraint of claim 1 further comprising a plurality of sensors on the main body with each sensor providing an indication in response to part of a patient touching the sensor, whereby an amount by which said patient extends outside of said field of view can be determined.

7. The constraint of claim 6 wherein each sensor is a contact sensor on an internal side of the main body.

8. The constraint of claim 1 wherein at least one of the main body and each coupler is made of carbon fiber or polyethylene.

9. The constraint of claim 1 further comprising a strap adapted to attach the main body to the bed or treatment pallet.

10. The constraint of claim 1 wherein the medical imaging procedure is at least one of a computerized tomography (CT), a Positron Emission Tomography (PET), Single Photon Emission Computed Tomography (SPECT), PET/CT, and SPECT/CT.

11. A constraint to constrain a patient with respect to a field of view of a medical imaging procedure, the constraint comprising:
    a main body having a substantially arcuate shape, a first end, and a second end, said main body being adapted to constrain said patient to lie within a determinable area with respect to said field of view, so as to reduce artifacts in image reconstruction; and
    at least one coupling means for coupling the main body to a bed or treatment pallet.

12. The constraint of claim 11 wherein the main body further comprises a main section having a first radius and two secondary sections having a second radius, with the main body interposed between the two secondary sections with the at least one coupling means at about a distal end of one of the secondary sections.

13. The constraint of claim 12 wherein the first radius is in the range of about twenty-five (25) to thirty (30) centimeters.

14. The constraint of claim 12 wherein the second radius is in the range of about twenty-five (25) to thirty (30) centimeters.

15. The constraint of claim 12 wherein the first radius of the constraint is sized to restrict a patient to lie within a field of view of said medical imaging procedure.

16. The constraint of claim 11 further comprising a plurality of sensors on the main body with each sensor providing an indication in response to part of a patient touching the sensor, whereby an amount by which said patient extends outside of said field of view can be determined.

17. The constraint of claim 16 wherein each sensor is a contact sensor on an internal side of the main body.

18. The constraint of claim 11 wherein at least one of the main body and each coupling means is made of carbon fiber or polyethylene.

19. The constraint of claim 11 further comprising a strap adapted to attach the main body to the bed or treatment pallet.

20. The constraint of claim 11 wherein the medical imaging procedure is at least one of a computerized tomography (CT), a Positron Emission Tomography (PET), Single Photon Emission Computed Tomography (SPECT), PET/CT, and SPECT/CT.

* * * * *